United States Patent [19]

Maxwell et al.

[11] Patent Number: 5,057,278
[45] Date of Patent: Oct. 15, 1991

[54] STERILE LOOP CALIBRATION SYSTEM

[75] Inventors: Thomas P. Maxwell, Santa Ana; Thomas G. Hacker, Anaheim, both of Calif.

[73] Assignee: Minnesota Mining and Manufacturing Company, St. Paul, Minn.

[21] Appl. No.: 514,704

[22] Filed: Apr. 26, 1990

[51] Int. Cl.$^5$ ............................................. G01N 21/00
[52] U.S. Cl. ...................................... 422/81; 422/68.1; 422/82.12; 422/102; 436/8; 436/11; 128/DIG. 12; 128/DIG. 13; 604/65; 604/67; 604/151
[58] Field of Search ..................... 422/63, 82.12, 102, 422/103, 81, 68.1; 417/476, 477; 604/151, 65, 67; 128/DIG. 12, DIG. 13; 436/8, 11

[56] References Cited

U.S. PATENT DOCUMENTS

| | | | |
|---|---|---|---|
| 2,002,862 | 5/1935 | Moran | 417/476 |
| 2,403,572 | 7/1946 | Wittenberg | 418/45 |
| 2,503,376 | 4/1950 | Burgess | 137/122 |
| 2,579,203 | 12/1951 | Putney | 261/3 |
| 2,585,440 | 2/1952 | Collins | 55/257.1 |
| 2,628,825 | 2/1953 | Kantor et al. | 261/140.1 |
| 3,334,657 | 8/1967 | Smith et al. | 137/888 |
| 3,874,850 | 4/1975 | Sorensen et al. | 436/50 |
| 3,884,640 | 5/1975 | Lock et al. | 422/82.03 |
| 4,119,406 | 10/1978 | Clemens | 422/81 |
| 4,266,941 | 5/1981 | Sullivan | 436/68 |
| 4,285,703 | 8/1981 | Alexander | 55/228 |
| 4,401,547 | 8/1983 | Schinkmann et al. | 204/415 |
| 4,424,276 | 1/1984 | Clark et al. | 435/50 |
| 4,443,407 | 4/1984 | Weinberg et al. | 422/82.04 |
| 4,516,580 | 5/1985 | Polanyi | 128/632 |
| 4,537,561 | 8/1985 | Xanthopoulos | 417/477 |
| 4,604,263 | 8/1986 | Smernoff | 422/50 |
| 4,640,820 | 2/1987 | Cooper | 422/82.04 |
| 4,668,634 | 5/1987 | Iwaski et al. | 436/68 |
| 4,764,315 | 8/1988 | Brusa | 261/140.1 |
| 4,830,013 | 5/1989 | Maxwell | 128/637 |
| 4,844,871 | 7/1989 | Polaschegg | 422/81 |

OTHER PUBLICATIONS

Soukhanou et al., Webster's II New Riverside University Dictionary, 1948, p. 341.

Primary Examiner—Robert J. Warden
Assistant Examiner—Theresa A. Trembley
Attorney, Agent, or Firm—Gary L. Griswold; Walter N. Kirn; Dale E. Hulse

[57] ABSTRACT

An endless path calibration system comprising a sensor cassette having a flow-through passage and at least one sensor to be calibrated, a chamber coupled to the sensor cassette to define an endless path and a sterile calibration liquid in the endless path. A gas injection passage for injecting gas into the sterile calibration liquid and a gas vent leading from the endless path to the exterior of the endless path. A check valve allows gas to escape from the endless path and substantially prevents gas and liquid from entering the endless path through the gas vent.

35 Claims, 5 Drawing Sheets

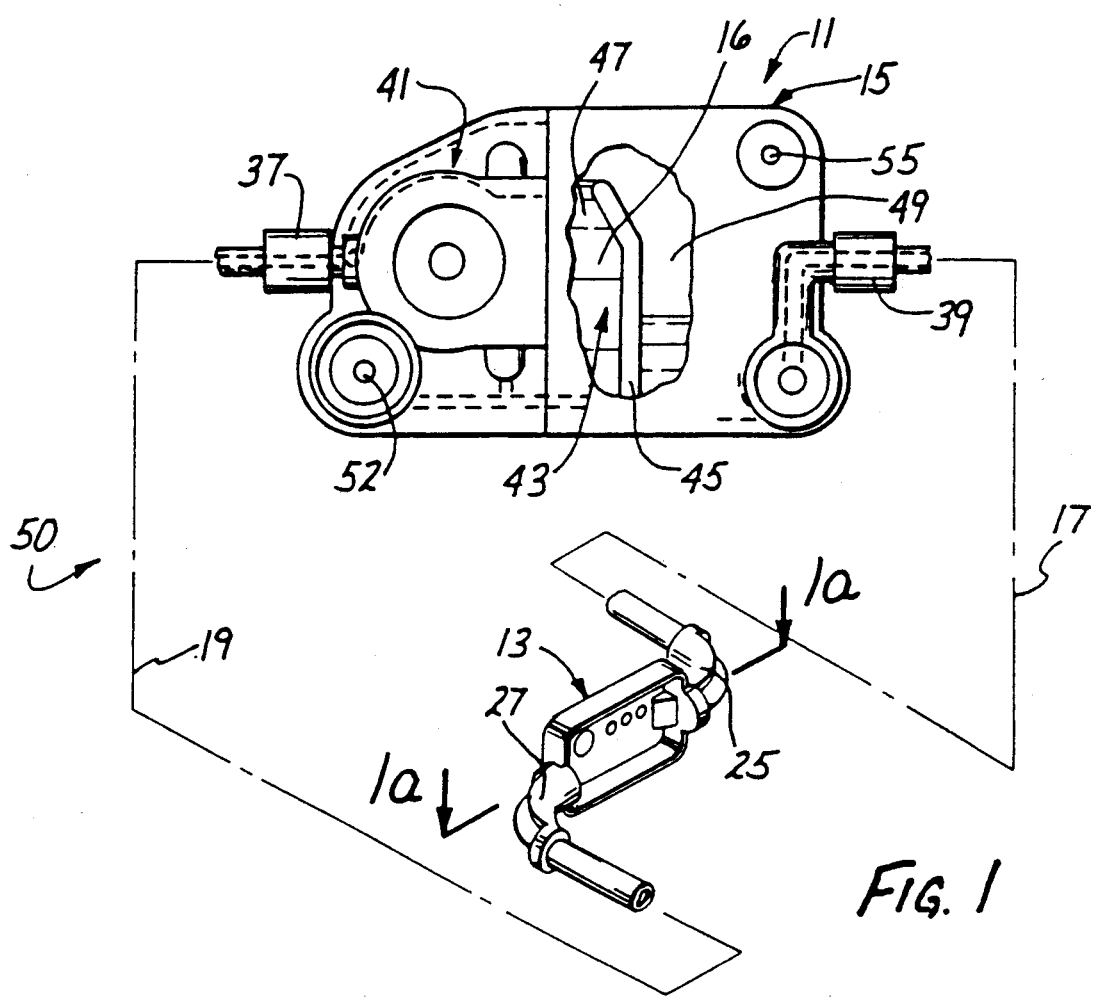
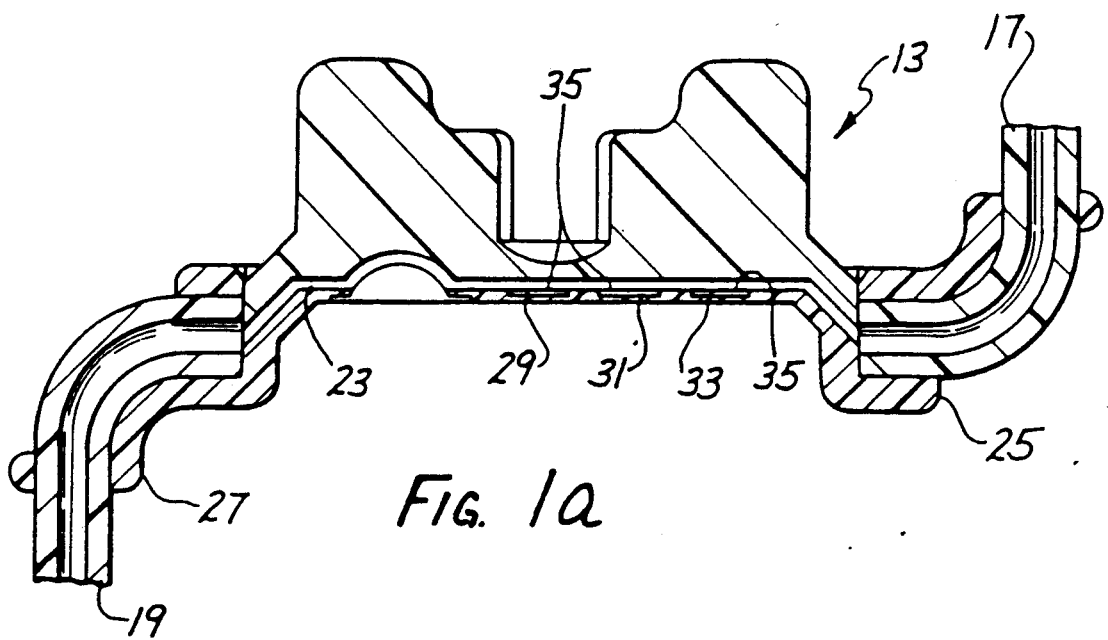

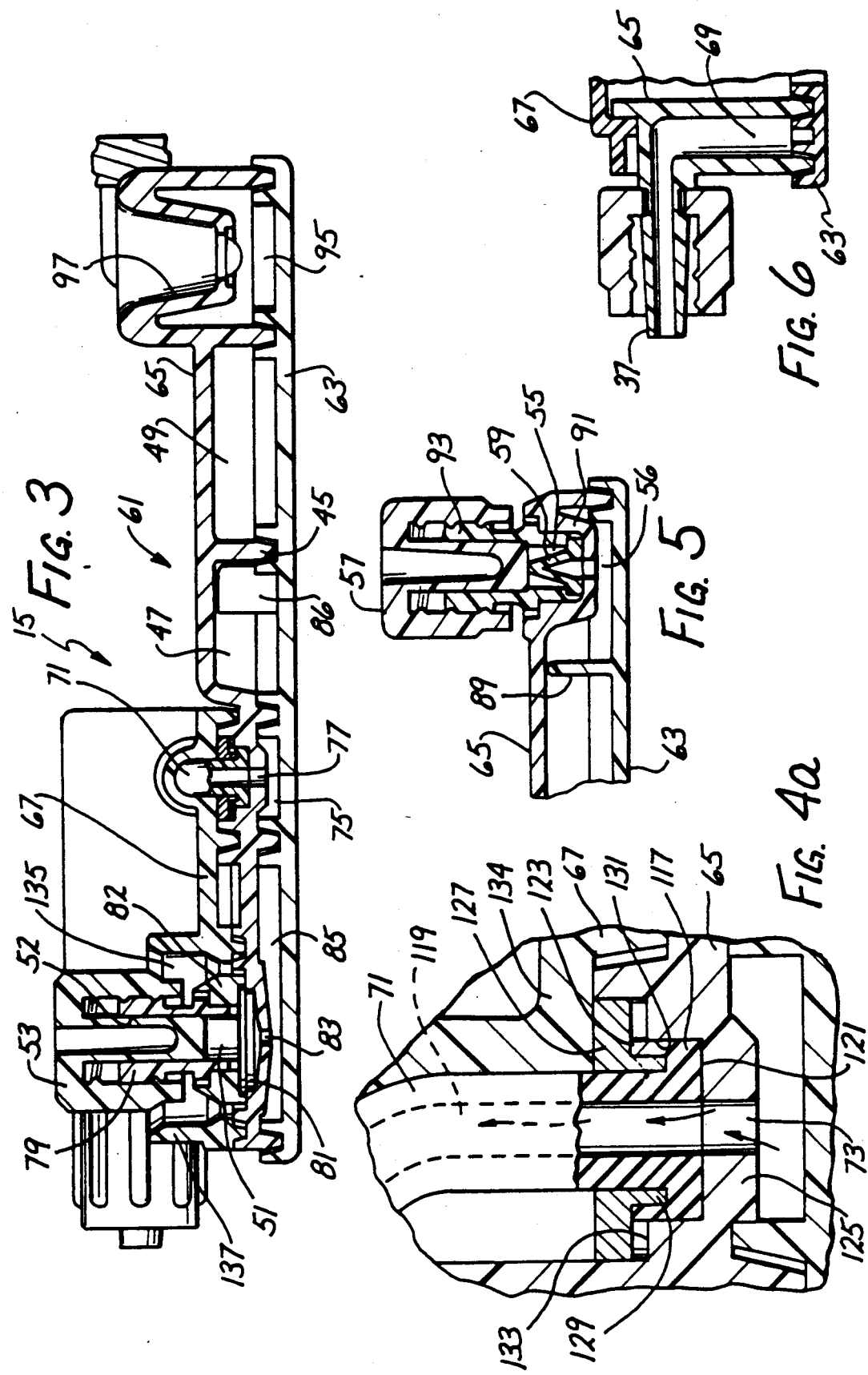

STERILE LOOP CALIBRATION SYSTEM

BACKGROUND OF THE INVENTION

It is often necessary or desirable to monitor various parameters of blood and to obtain quantitative data concerning such parameters in real time. In order to accomplish this, blood is caused to flow through a flow-through housing past sensors which provide signals representative of the parameters of interest. For example, Cooper U.S. Pat. No. 4,640,820 shows a flow-through housing with fluorescent sensors which respond to the partial pressure of oxygen, the partial pressure of carbon dioxide and the pH of blood which has passed through the flow-through housing.

Prior to using the flow-through housing, the sensors must be calibrated. One calibration technique, which is used for the sensors of the Cooper patent, is to attach the sensor carrier to a calibration housing containing calibration liquid. This places the sensors in communication with a relatively large cross-sectional area passage. The gas or gases of interest are then bubbled through the calibration liquid. A similar technique is utilized to calibrate the sensors shown in Maxwell U.S. Pat. No. 4,830,013.

This calibration technique, which employs an essentially static calibration liquid, is most satisfactory when used in conjunction with sensors adjacent a passage of sufficient cross-sectional area so that the calibration liquid remains in the passage while the gases are passed through the liquid. Because the sensors must be kept wet, a gas-only calibration technique cannot be employed.

For some applications, it is desirable to utilize a flow-through housing having a relatively small cross-sectional area and to maintain that area sterile during calibration. In fact, the cross-sectional area is sufficiently small so that, when gas is passed through the liquid, the surface tension may cause the calibration liquid to be expelled from the passage and prevent exposure of the sensors to the gases in the calibration liquid and thus cause an inaccurate calibration.

SUMMARY OF THE INVENTION

This invention solves the problems identified above. With this invention, sterile calibration liquid is equilibrated with the gas of interest and then pumped through the flow-through passage, thereby assuring that adequate calibration liquid will fill the flow-through passage. In addition, the sterile calibration liquid is pumped through a sterile-loop calibration system. The sterile calibration loop provides an endless path for circulation of the sterile calibration liquid. The provision of an endless path eliminates the need to replenish the calibration liquid supply and the need to dump any of the liquid to drain. This also enhances the sterility of the calibration operation. In addition, openings in the loop which could cause a break in the sterility barrier are minimized.

The commonly used blood gas sensors sense oxygen and carbon dioxide, respectively. In order to calibrate $O_2$ and $CO_2$ sensors, it is necessary to control, i.e., raise or lower, the partial pressures of these two gases in the calibration liquid until they reach a known desired level. With this invention, this is brought about by injecting a sterile gas into the sterile loop. The sterile gas contains known percentages by volume of oxygen and $CO_2$.

The sterile gas is mixed with the sterile calibration liquid in the sterile loop to adjust or control the partial pressure of at least a component, e.g., $O_2$ or $CO_2$, of the gas in the sterile calibration liquid. To enable a continuous supply of fresh gas without an undesirable pressure build up in the loop, the gas is vented from the sterile loop. By pumping the sterile calibration liquid having the $CO_2$ and $O_2$ dissolved therein through the sterile loop and exposing the sensors to this calibration liquid, calibration can occur using known techniques.

More specifically, the sterile-loop calibration system includes a sensor cassette having a flow-through passage and including at least one sensor to be calibrated. The sensor is responsive to a characteristic of a gas, such as the partial pressure of $O_2$ or $CO_2$. The flow-through passage forms a portion of the sterile loop. To further guard against loss of sterility, a sterile calibration liquid is provided in the sterile loop at the factory so that the user need not do this.

To accomplish gas injection, a gas injection passage is provided through which a gas can be injected into the sterile calibration liquid. To control the partial pressures of the gases of interest in the sterile calibration liquid to a desired level, means is provided in the sterile loop for mixing the gas and the calibration liquid. Although such means may take different forms, it may advantageously include a region, such as a chamber, in the sterile loop of increased volume which reduces flow velocity and, therefore, provides more time for equilibration. To accomplish venting of the gas, a gas vent leading from the sterile loop to the exterior of the sterile loop is provided.

Sterility through the vent can be provided in different ways. For example, means may be provided in the vent for allowing gas to escape from the sterile loop and to substantially prevent gas and/or liquid from entering the sterile loop through the gas vent. Alternatively, or in addition thereto, the vent may include or define a small area flow-restricting orifice. If no check valve is used, the orifice should be closed or covered after calibration. Sterility can also be enhanced by maintaining the pressure in the loop above atmospheric so that there is a differential pressure across the gas vent tending to allow gas to escape and precluding gas entry through the vent into the sterile loop.

If desired, a source of sterile gas may be provided for injection into the sterile loop through the gas-injection passage. However, preferably, a gas-sterilizing filter is provided in communication with the gas injection passage for sterilizing the gas injected into the sterile loop. This eliminates the need for providing a separate source of sterilized gas at the user's facility.

The chamber preferably includes a sparging chamber section and a settling chamber section. The sparging chamber serves primarily as a mixing chamber and provides time for the partial pressure of the gases of interest to equilibrate to the desired level. In the settling chamber, bubbles are given an opportunity to rise to the top and be vented. Accordingly, the vent preferably terminates in the settling chamber. In one preferred construction, the chamber includes a weir or divider which divides the chamber into the sparging chamber section and the settling chamber section. A baffle adjacent the weir and in the sparging chamber can advantageously be provided for optimizing bubble size in the calibration liquid.

In a preferred construction, the gas is injected into the calibration liquid in the sterile loop upstream of the chamber and then passed to the chamber. This provides some opportunity for mixing of the gas and the liquid before they reach the chamber and helps to provide relatively small gas bubbles in the chamber. Preferably, the gas-injection passage is oriented relative to the sterile loop so that the gas is directed into the sterile loop substantially at a location in the sterile loop where the flow of sterile calibration liquid is changing direction. This can be accomplished, for example, by a "T" connection.

The sterile loop of this invention is preferably a closed liquid loop in that no liquid is added to the loop during operation, and little, or essentially no, liquid is drained from the loop. Although a gas is added and vented and some small quantity of liquid may escape through the vent, it is relatively easy to assure that the gas is sterile by using the sterilizing filter, and the venting of the gas and possibly small amounts of liquid through an orifice or a check valve help maintain the loop effectively closed. Moreover, there is no need to collect the vented gas.

In a preferred construction, a number of the components of the calibration system can be provided within, or as a part of, a calibration housing. The calibration housing has an inlet, an outlet and a liquid passage extending through the housing from the inlet to the outlet. Conduit means couples the opposite ends of the flow-through passage of the sensor cassette to the inlet and the outlet, respectively, of the housing to form the sterile loop. The chamber, gas injection passage and gas vent are all provided on the housing.

It is desirable to monitor the temperature of the calibration liquid and to maintain it at a desired temperature. For this purpose, the housing has a temperature sensing location, which can advantageously be a temperature well, adapted to cooperate with a temperature probe. Although the temperature well can be in heat-exchange relationship with any part of the sterile loop, preferably it is in heat exchange relationship with an outlet passage section leading from the settling chamber to the outlet of the housing. This location keeps the temperature sensor well on the housing and as close to the sensor cassette as possible.

In a preferred construction, the cuvette passage includes a radially compressible tube which is progressively compressed in a manner to achieve peristaltic pumping action. The tube is wrapped in a circumferential direction at least part way around the tube compressor. The tube has opposite end portions which extend generally tangentially of the tube compressor and then axially of the tube compressor to their respective ends. By turning the end portions of the tube to extend generally axially of the tube compressor, the number of parts required for the housing are reduced, assembly is facilitated and the space required for the housing is reduced.

However, because the end portions of the tube are turned in this fashion, it is necessary to seal the ends of the tube to other portions of the housing. More particularly, the liquid passage includes first and second passage sections, and means is provided for sealing the ends of the tube to the first and second passage sections, respectively. In a preferred form, this seal construction employs a rigid ring which is loaded against a deformable flange of the tube by a portion of the housing which contacts the rigid ring around less than 360 degrees to squeeze the flange and achieve the desired seal.

Another feature of this invention is a novel seal construction for sealing the ends of this tube to portions of the housing.

The invention, together with additional features and advantages thereof, may best be understood by reference to the following description taken in connection with the accompanying illustrative drawing.

BRIEF DESCRIPTION OF THE DRAWING

FIG. 1 is a schematic illustration of a sterile-loop calibration system constructed in accordance with the teachings of this invention.

FIG. 1A is a sectional view taken generally along line 1A—1A of FIG. 1 and illustrating one form of sensor cassette.

FIGS. 3 and 4 are enlarged sectional views taken generally along lines 3—3 and 4—4, respectively, of FIG. 2.

FIG. 4A is an enlarged fragmentary sectional view of a portion of FIG. 4 illustrating a preferred form of the novel seal construction of this invention.

FIG. 5 is an enlarged fragmentary sectional view taken generally along line 5—5 of FIG. 2.

FIG. 6 is an enlarged fragmentary sectional view taken generally along line 6—6 of FIG. 2.

DESCRIPTION OF THE PREFERRED EMBODIMENT

Figure 7:
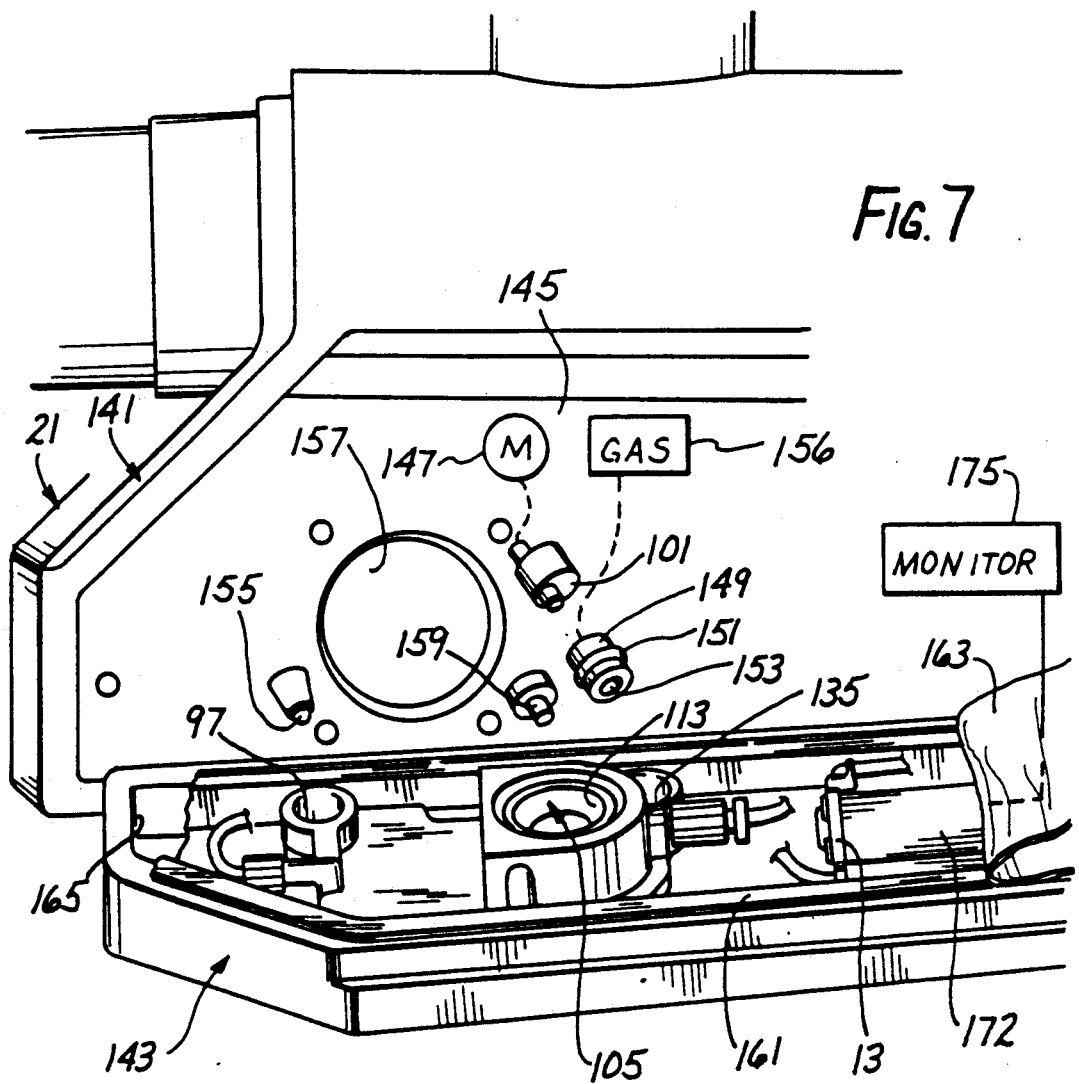
FIG. 7 is a fragmentary perspective view illustrating the calibration system and, in particular, the calibration apparatus, with the housing in a package and the door of the calibration apparatus in the open position.

FIG. 1 shows a sterile-loop calibration system 11 which generally comprises a sensor cassette 13, a calibration housing 15, sterile calibration liquid 16, and conduit means, including conduits 17 and 19, for coupling the calibration housing to the sensor cassette. Not illustrated in FIG. 1, but also included in the calibration system, is a calibration apparatus 21 (FIG. 7). The portion of the system shown in FIG. 1 is a disposable component or apparatus and is designed for use with the calibration apparatus 21, which is a reusable component.

The sensor cassette 13 may be of the type shown in common assignee's co-pending application Ser. No. 229,617 filed on Aug. 8, 1988, and entitled Intravascular Blood Gas Sensing System, which is incorporated by reference herein. Briefly however, the sensor cassette 13 includes a flow-through passage 23 (FIG. 1A) having first and second ends in the form of tube fittings 25 and 27 which are joined to the conduits 17 and 19, respectively. Sensors 29, 31 and 33, which are to be calibrated, are carried by the sensor cassette in communication with the flow-through passage 23. The sensors 29, 31 and 33 may be, for example, for sensing carbon dioxide, pH and oxygen, respectively, and each of these sensors is covered by a membrane 35 which is permeable to the constituent of interest as described in application Ser. No. 229,617 referred to above. The flow-through passage 23 has a very small cross-sectional area and may be, for example, rectangular and have dimensions of about 0.015 inch×0.164 inch.

The calibration housing 15 (FIGS. 1 and 2) has an inlet 37, an outlet 39 and a liquid passage 41 extending through the housing from the inlet to the outlet. The liquid passage 41 includes a chamber 43, which is divided by a weir 45 or divider into a sparging chamber section 47 and a settling chamber section 49.

The flow-through passage 23, the conduits 17 and 19, and the liquid passage 41 form a sterile loop which provides an endless loop in which the sterile calibration liquid 16 can be circulated.

Figure 2:
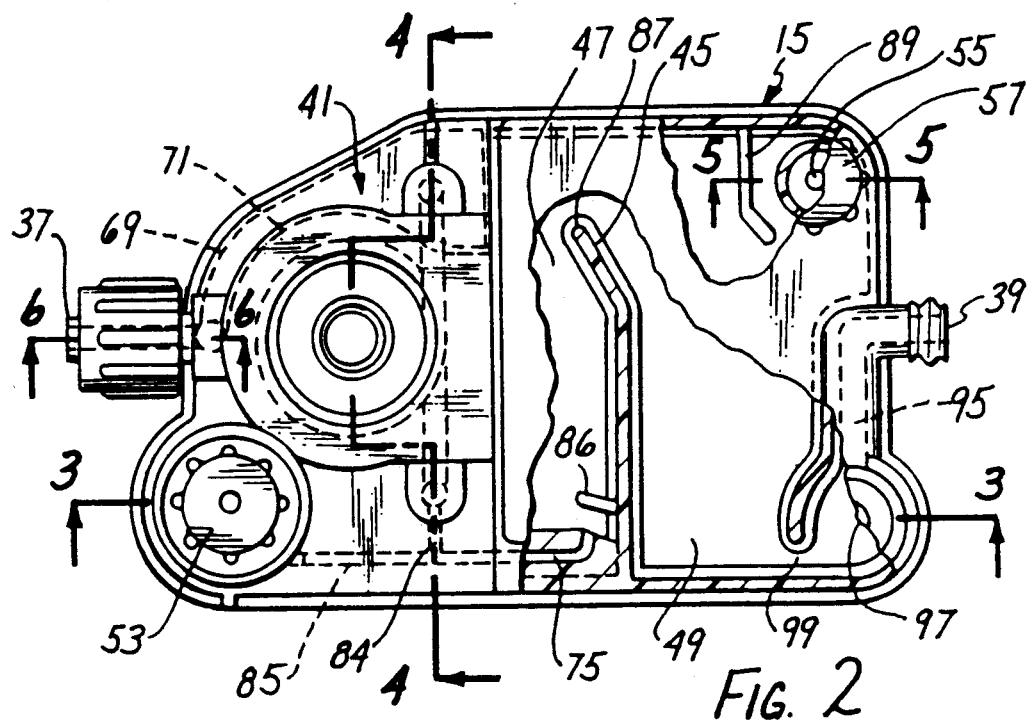
FIG. 2 is a plan view with portions broken away of a preferred form of calibration housing constructed in accordance with the teachings of this invention.

The housing 15 has a gas injection passage 51 leading from a gas injection port 52 to a location in the liquid passage 41 for injecting gas into the liquid passage and means in the form of a threaded closure cap 53 (FIGS. 2 and 3) for closing the gas-injection port. The housing 15 also includes a gas vent 55 which, in this embodiment, includes a restricted orifice 56 having, for example, a diameter of about 1/16 inch. The gas vent 55 leads from the settling chamber 49 to the exterior of the housing. The gas vent 55 may be completely closed by a closure cap 57 (FIGS. 2 and 5). A check valve 59 (FIG. 5) in the gas vent 55 allows gas to escape from the settling chamber 49 and substantially prevents gas from entering the chamber through the gas vent 55.

The construction of the housing 15 can best be understood by reference to FIGS. 2-6. Although various constructions are possible, as shown in FIG. 3, the housing 15 includes a housing 61 of multiple molded plastic components, such as a base 63, a cover 65 and a top section 67. At least the cover 65 and the top section 67 are preferably transparent. The base 63, the cover 65 and the top section 67 may be suitably coupled together as with an adhesive.

As shown in FIGS. 2 and 6, the inlet 37 leads to an inlet passage section 69 of the liquid passage 41. A radially compressible tube 71 (FIG. 4) communicates with the inlet passage section 69 through an aperture or opening 73 in the cover section 65 and with a chamber inlet section 75 (FIGS. 2 and 4) through an aperture or opening 77 (FIG. 4) which also is in the cover 65. The chamber inlet section 75 leads to the sparging chamber 47 as shown in FIG. 2.

The gas injection passage 51 (FIG. 3) is defined in part by an externally threaded tube 79 affixed to the top section 67. A gas-sterilizing filter 81 is supported on the cover 65 and retained in place by a spider section 82 of the top section 67. The gas-sterilizing filter 81 may be, for example, a 0.2 micron pore filter which is capable of sterilizing gas which passes through it due to the small pore size. Accordingly, with the cap 53 removed, a non-sterile gas can be introduced as described below to the injection port 52 whereby it will pass through the filter 81, an aperture 83 in the cover 65, and a passage section 85 of the gas injection passage between the base 63 and the cover 65 to the chamber inlet section 75 as shown in FIGS. 2 and 3. The chamber inlet section 75 forms a right angle (FIG. 2), and the passage section 85 enters the apex of the right angle to form a "T" 84. Thus, the gas is injected into the liquid at a location where the direction of flow of the liquid is changing. For example, the gas injected into the gas injection passage 51 may comprise $CO_2$, $O_2$ and an inert gas, such as nitrogen.

With this construction, the sterile calibration liquid 16, with the gas therein, is introduced into the sparging chamber 47. The "T" 84 provides a premixing of the gas and liquid. As shown in FIG. 2, the base 63 preferably has a baffle 86 adjacent the weir 45 and above the location where the chamber inlet section 75 opens into the sparging chamber 47 for the purpose of breaking up larger bubbles that may exist in the liquid. The sparging chamber 47 provides time for the gas to equilibrate in the calibration liquid 16, and as liquid fills the sparging chamber, it is allowed to flow over the free end 87 of the weir 45 and fall into the settling chamber 49. As gas bubbles through the calibration liquid 16 in the sparging chamber 47, foam is generated and also flows over the weir 45 into the settling chamber 49. In the settling chamber 49, any remaining gas bubbles are given another opportunity to rise to the top and be vented through the vent 55, which is in the form of an aperture in the cover 65 as shown in FIG. 5. A baffle 89 may be provided adjacent the vent 55 to reduce the likelihood that the liquid component of any foam will exit through the vent 55.

Although various constructions are possible, in the form shown in FIG. 5, the check valve 59 is conventional and is retained in a recess 91 in the cover 65 by an externally threaded tube 93 affixed to the cover. The cap 57 is threadedly attached to the tube 93.

As shown in FIG. 2, the liquid passage 41 also includes an outlet passage section 95 leading from the settling chamber 49 to the outlet 39. The housing 15 has a temperature sensing location which, in this embodiment, is in the form of a temperature well 97 adapted to receive a temperature probe in heat exchange relationship with the outlet passage section 95 as shown in FIG. 3. Although various constructions are possible, the outlet passage section 95 may communicate with the settling chamber 49 through an aperture 99 as shown in FIG. 2. The aperture 99 is positioned to force flow to occur around the temperature well 97.

In order to move the calibration liquid 16 through the sterile loop, it is necessary to provide a pump to force the calibration liquid through the sterile loop 50. The pump includes pump components in the housing 15 and an external rotary input or rotary driving element 101 (FIG. 7) which is part of the calibration apparatus 21. The pump components in the housing 15 include a curved wall surface 103 (FIG. 4), the compressible tube 71 and a tube compressor 105. The opposite ends of the tube 71 form an inlet and an outlet, respectively, for the pump.

More particularly, the wall surface 103 in this embodiment is cylindrical and constitutes the inner surface of a cylindrical boss 107, portions of which are formed integrally with the cover 65 and the top section 67. The tube compressor 105 is surrounded by the wall surface 103, and the tube 71 is wrapped in a circumferential direction about one time around the tube compressor and lies between the tube compressor and the wall surface 103.

The cover 65 and the top section 67 have flanges 109 and 111, respectively, which provide retaining surfaces for restraining the tube compressor 105 against axial movement relative to the wall surface 103. Because there is a radial clearance between the tube compressor 105 and the wall surface 103 and because the flanges 109 and 111 do not restrain the tube compressor against radial movement, the tube compressor is mounted on the housing for free radial movement relative to the wall surface 103 and the boss 107. In other words, the tube compressor 105 can be moved radially in any direction from the centered or neutral position shown in FIG. 4, with the only consequence being the squeezing of the compressible tube 71. With this construction, the tube compressor 105 can be caused to roll along the tube 71 to squeeze the tube in a zone which moves along the tube to thereby pump fluid in the tube. In the neutral position, the tube 71 is not squeezed.

The tube compressor 105 is generally cylindrical and tubular and has an outwardly opening cavity 113 having a mouth 115 which is flared radially outwardly to receive the rotary input 101 as described hereinbelow. Thus, the cavity 113 provides means on the tube compressor 105 for use in releasably drivingly coupling the tube compressor to the external rotary element 101 whereby the tube compressor can be rolled along the tube 71 to pump fluid in the tube. The tube compressor 105 is constructed of a suitable rigid material, such as a rigid plastic, and the cavity 113 is defined by a smooth, hard, low-friction surface which surface is smoother, harder and of substantially lower friction than the tube 71. This facilitates reception of the rotary driving element 101, which is also smooth and hard and provides a low-friction surface.

The tube compressor 105 also has an annular flange 116 at the opening of the mouth 115. The flange 116 cooperates with the flange 109 to close the upper end of a compartment 118 between the tube compressor 105 and the wall surface 103 so that the tube 71 cannot escape out the upper end of the compartment regardless of the radial position of the tube compressor 105.

Figure 4:
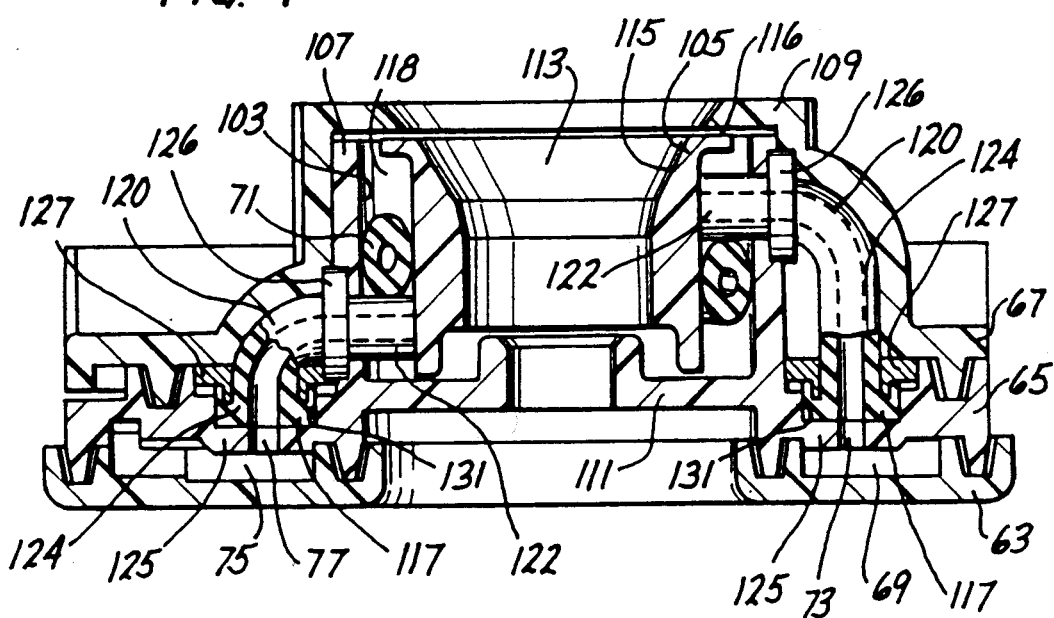

The tube 71 has opposite end portions 120 having regions 122 which extend generally tangentially of the tube compressor 105 and regions 124 which extend axially of the tube compressor 105 to their respective ends. Each set of the regions 122 and 124 is integrally joined by a 90-degree bend portion. The tangential regions 122 have annular flanges 126 which are captured as shown in FIG. 4 by the boss 107 and adjacent regions of the top section 67 to thereby hold the tube 71 in position.

To prevent leakage of the sterile calibration fluid, it is important to seal the opposite ends of the tube 71 to the confronting portions of the cover 65. This can advantageously be accomplished with the seal construction shown in FIG. 4A. As shown in FIG. 4A, the tube 71 has an annular flange 117 at each end and a tube passage 119, which forms a portion of the liquid passage 41, extending longitudinally through the tube and opening at its opposite ends. The tube 71 and its flanges 117 are constructed of a resilient elastomeric material, such as silicone rubber, and as such are deformable. Each of the flanges 117 has an outer face 121 and an inner face 123.

The cover 65 has flange-supporting faces 125 surrounding the apertures 73 and 77, respectively. The outer face 121 of each of the flanges 117 engages the associated flange-supporting face 125 with the apertures 73 and 77 being in registry with the passage 119.

The tube 71 is received by a rigid clamp ring 127 of metal or rigid plastic and by a portion of the top section 67, and these members cooperate to form a tube-receiving structure which is coupled to the cover 65. The clamp ring 127 has an annular projection 129 which engages the inner face 123. The annular projection 129 is radially narrower than the inner face 123 of the flange 117 and provides high-unit loading of the flange to deform the flange. The annular projection 129 urges the flange 117 tightly against the supporting face 125 to provide a fluid-tight seal along the juncture of the tube passage 119 and the aperture 73. The top section 67, when coupled to the cover 65, urges the clamp ring 127 toward the flanges 117. As shown in FIG. 4A, the annular projection 129 deforms the flange 117 with some of the material of the flange flowing upwardly around the annular projection. In its undeformed configuration, the inner face 123, as well as the outer face 121, are planar, although a planar configuration is not required.

The cover 65 has wells 131 for receiving the flanges 117, with the flange-supporting faces 125 being at the end or bottom of the associated wells. The wells 131 open at circumscribing surfaces 133, and the clamp rings 127 are spaced from the surfaces 133, respectively. With this construction, all of the force applied to the clamp rings 127 by the top section 67 is used to deform the associated flange 117 to effect a tight seal, and none of this force is taken up by the underlying surfaces 133.

More specifically, the top section 67 has a shoulder 134 which contacts the clamp ring 127 to force it downwardly (as viewed in FIG. 4a) against the flange 117. The shoulder 134 contacts the clamp ring 127 around less than 360 degrees, and in the embodiment illustrated, this contact region is a little over 180 degrees. However, because the clamp ring 127 is rigid, it operates to apply a squeezing force to the flange 117 around a full 360 degrees of the flange.

As shown in FIGS. 2-4, the gas-injection port 52, the temperature well 97 and the tube compressor 105 all open at the exterior of the housing on the same side of the housing. In addition, the housing 15 has a well 135 defined by an upstanding annular boss 137, and the well also opens on the same side of the housing. The well 135 surrounds the gas-injection port 52.

Figure 8:
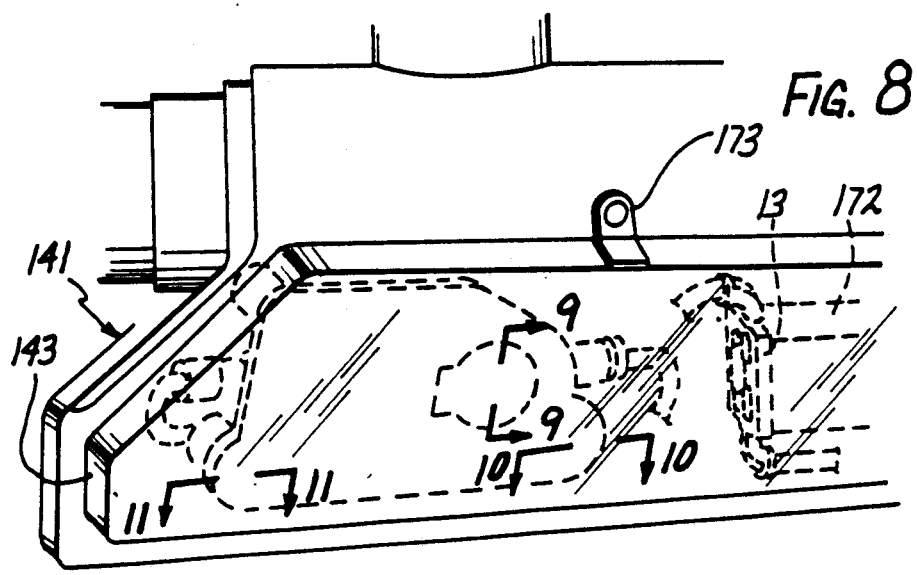
FIG. 8 is a perspective view similar to FIG. 7, with the door in the closed position.
Figure 9:
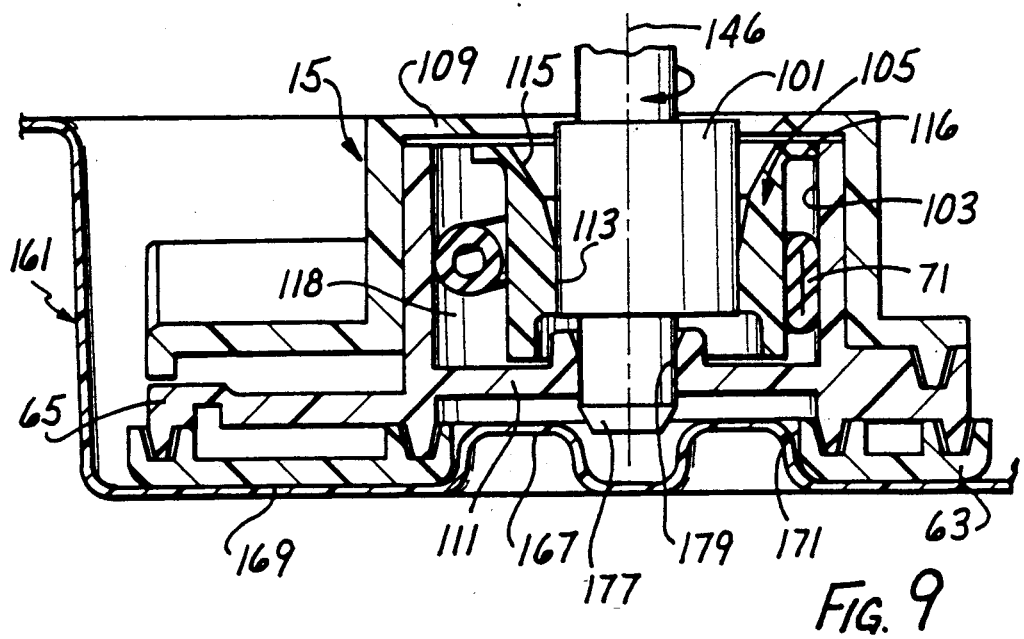
FIGS. 9, 10 and 11 are enlarged fragmentary sectional views taken generally along lines 9—9, 10—10 and 11—11, respectively, of FIG. 8.

The calibration apparatus 21 includes a supporting structure 141 and a door 143 pivotally mounted on the supporting structure for movement between an open position shown in FIG. 7 and a closed position shown in FIG. 8. The rotary driving element 101 is rotatably mounted on the supporting structure 141 and projects outwardly from a front surface 145 thereof. The rotary driving element 101 is an eccentrically mounted cam which is rotatable about an axis 146 (FIG. 9). In this embodiment, the rotary driving element 101 is driven by a suitable motor 147, which is also carried by the supporting structure 141. The rotary driving member 101 serves as a cam to move the tube compressor 105 to bring about a pumping action in the tube 71.

A tube 149 carrying an annular seal 151 and defining a gas exit port 153 is mounted on the supporting structure 141 and projects outwardly from the front surface 145 in the same direction as the rotary driving element 101. A temperature sensor in the form of a temperature probe 155 is also mounted on the supporting structure 141 and projects outwardly from the front surface 145 in the same direction as the rotary driving element 101. The tube 149 is coupled to a source 156 of calibration gas, which also may be carried by the supporting structure 141. The temperature probe 155 may be coupled to an appropriate temperature read out (not shown) and-/or to a circuit for controlling a heat lamp 157 which is carried by the supporting structure 141 and faces outwardly from the front surface 145 in the same direction as the rotary driving element 101. The heat lamp 157 is provided for the purpose of maintaining the calibration liquid 16 at the desired temperature, such as 37 degrees C.

A spring-biased ejector 159 is mounted on the supporting structure 141 and projects outwardly from the front surface 145. When the housing 15 is positioned on the supporting structure 141 as described below and the door is in the closed position of FIG. 8, the ejector 159 applies a resilient force to the housing to urge the door toward the open position of FIG. 7.

The entire disposable component of the system 11 as shown in FIG. 1 is carried in an openable package 161 (FIGS. 7 and 9). The package 161 includes a cover 163 which can be peeled back as shown in FIG. 7 to expose the portions of the system 11 carried by the package. The door 143 has a recess 165 for receiving the package 161. The package 161 and the recess 165 have sufficiently complementary configurations so that the recess can at least assist in releasably retaining the package in a predetermined orientation. The housing 15 is retained within the package 161 in a predetermined orientation by a projection 167 in a bottom wall 169 of the package 161 and a mating recess 171 (FIG. 9) in the housing.

In use, the cover 163 is peeled back from the remainder of the package 161, and the package is placed in the recess 171 of the door 143 as shown in FIG. 7. An optical head 172 is coupled to the sensor cassette 13 in a known manner to optically couple the sensors 29, 31 and 33 to an instrument or monitor 175. The closure caps 53 and 57 are removed to expose the gas injection port 52 and the gas vent 55, respectively. The door 143 is then pivoted from the open position of FIG. 7 to the closed position of FIG. 8, and the door is retained in the closed position by a suitable lock 173.

Placing the door 143 in the closed position positions the housing on the supporting structure 141. When so positioned, the rotary driving element 101, the tube 149 and the temperature probe 155 are received in the cavity 113, the well 135 and the temperature well 97, respectively, and this results automatically from simply closing the door, i.e., moving the door to the closed position. In addition, the ejector 159 is resiliently compressed against a region of the housing 15 so that the ejector resiliently loads the door 143 toward the open position of FIG. 7.

The flared mouth 115 serves as a cam follower or lead in as the rotary driving element 101 is inserted into the cavity 113. Specifically, the rotary driving element 101 cooperates with the flared mouth 115 to cam the tube compressor 105 radially to the position shown, by way of example, in FIG. 9 in which one side of the tube 71 is tightly squeezed between the tube compressor and the curved wall surface 103, and the other side of the tube 71 is uncompressed.

The rotary driving element 101 has a nose 177 (FIG. 9) which is received in a bearing 179 when the door is in the closed position.

It will be appreciated that the tube compressor 105 is in the neutral position during storage of the housing 15 and at all times when the rotary driving element 101 is not received within the tube compressor 105 as shown in FIG. 9. Consequently, the tube 71 is normally not compressed, or significantly compressed. Consequently, there is no danger of the tube 71 taking a "set" or becoming occluded as a result of compression of the tube during storage. Because the tube compressor 105 is free to move radially inside the curved wall surface 103, eccentric rotation of the rotary driving element 101 about the axis 146 (FIG. 9) causes the tube compressor 105 to roll along the tube to create a peristaltic pumping action to pump the calibration liquid 16 through the sterile loop 50 including the flow-through passage 23 of the housing 15. Because the surfaces defining the cavity 113 and the exterior of the rotary driving element 101 are relatively hard, smooth and of low friction, the insertion of the rotary driving element 101 into the cavity 113 is easily accomplished by simply closing the door 143 even though a camming action and consequent radial movement of the tube compressor 105 must occur.

It should be noted that no angular indexing of the rotary driving element 101 is necessary in order to insert the rotary driving element into the cavity 113 of the tube compressor 105. Thus, driving engagement can be established between the rotary driving element 101 and the tube compressor 105 automatically as a result of moving the door 143 to the closed position and regardless of the angular orientation of the rotary driving element 101.

Figure 10:
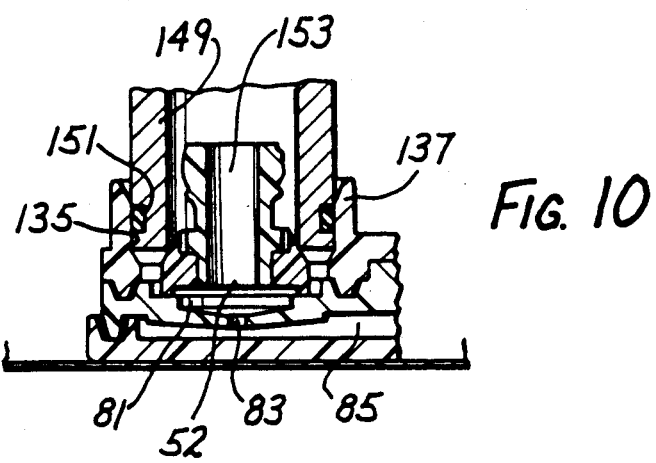
Figure 11:
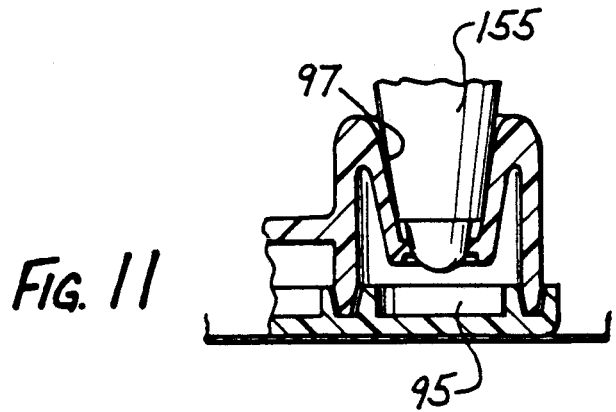

The closing of the door 143 also inserts the tube 149 into the well 135 to place the gas exit port 153 in communication with the gas injection port 52 as shown in FIG. 10. The seal 151 cooperates with the well 135 to maintain a gas-tight seal between the tube 149 and the boss 137 over a range of insertion depths. Consequently, gas can be supplied from the gas source 156 through the gas exit port 153, the gas injection port 52, the passage section 85 (FIG. 2) to the chamber inlet section 75 at the "T" 84. The gas is supplied at some positive pressure, and consequently, the pressure in the liquid passage 41 is greater than ambient. For this reason, gas vents from the gas vent 55, and the positive pressure existing in the liquid passage 41 and the flow of gas outwardly inhibits inward flow of gas or liquid through the gas vent 55 into the liquid passage 41. At the "T" 84, the gas is introduced into the stream of calibration liquid 16 being circulated by the pump and is premixed with the liquid for introduction into the sparging chamber 47. The gas is sterilized by the filter 81 so that sterile gas is introduced into the sterile calibration liquid 16. Gas which vents from the vent 55 can escape from within the calibration apparatus 21.

In the closed position of the door 143, the temperature probe 155 is received within the well 97 so that temperature readings can be taken of the liquid in the outlet passage section 95. In addition, the heat lamp 157 is placed in close proximity with the housing 15 so that the calibration liquid 16 can be heated to the desired temperature.

When the partial pressures of the gases of interest reach the desired level in the calibration liquid 16, the monitor 175, is calibrated to the particular sensor cassette 13 and, particularly, the sensors 29, 31 and 33 thereof using conventional techniques. Thereafter, lock 173 is unlocked, and the door 143 is pivoted to the open position by the ejector 159 to remove the housing 15 from the calibration apparatus 21. The sensor cassette 13 can be employed with the monitor 175 for the measurement of the relevant blood parameters of interest of a patient as disclosed, for example, in application Ser. No. 229,617 referred to above.

Although an exemplary embodiment of the invention has been shown and described, many changes, modifications and substitutions may be made by one having ordinary skill in the art without necessarily departing from the spirit and scope of this invention.

We claim:

1. A sterile-loop calibration system comprising:
   a sensor cassette having a flow-through passage and including at least one sensor to be calibrated, said sensor being responsive to a characteristic of a gas;
   means defining a chamber;

means including said flow-through passage and said chamber for defining a closed, endless loop;

a sterile calibration liquid in said endless loop, said endless loop providing an endless path for circulation of the sterile calibration liquid whereby no calibration liquid is added to the endless loop and substantially little or no calibration liquid is drained from the endless loop during operation;

a gas injection passage through which a gas can be injected into the sterile calibration liquid in said endless loop;

means in said endless loop for mixing the gas and the sterile calibration liquid whereby the sterile calibration liquid and the gas can be circulated through the endless loop to thereby permit calibration of the sensor; and a gas vent leading from said endless loop to the exterior of the endless loop.

2. A system as defined in claim 1 including gas sterilizing filter means in communication with the gas injection passage for sterilizing the gas injected into the loop.

3. A system as defined in claim 1 wherein said mixing means includes said chamber.

4. A system as defined in claim 3 wherein said chamber includes a divider which divides said chamber into a sparging chamber section and settling chamber section, and said gas vent terminates in said settling chamber section.

5. A system as defined in claim 4 including a baffle adjacent the divider and in the sparging chamber section for breaking up bubbles in the sterile calibration liquid.

6. A system as defined in claim 1 wherein the loop is configured to change the direction of flow of the sterile calibration liquid at one location and the gas is directed into the loop substantially at said one location.

7. A system as defined in claim 1 including a pump for circulating the sterile calibration liquid in the loop.

8. A system as defined in claim 7 wherein the pump has an inlet and an outlet, said mixing means includes said chamber and the chamber has an inlet and an outlet, and the gas injection passage introduces the gas into the sterile calibration liquid between the inlet to the chamber and the pump outlet.

9. A system as defined in claim 1 wherein the gas vent includes a restricted orifice.

10. A system as defined in claim 1 including means in the gas vent for allowing gas to escape from the loop and to substantially prevent gas from entering the loop through the gas vent.

11. A sterile-loop calibration system comprising:
a sensor cassette having a flow-through passage and including at least one sensor to be calibrated, said flow-through passage having first and second ends;
a calibration housing having an inlet, an outlet, and a liquid passage extending through the housing from the inlet to the outlet;
conduit means for coupling the first and second ends of the flow-through passage of the sensor cassette to the inlet and outlet, respectively, of the housing to form a loop which provides an endless path;
said liquid passage including a chamber;
said housing having a gas injection passage leading to a location in said liquid passage for injecting gas into the liquid passage and means for closing said gas injection passage; and
said housing including a gas vent leading from said chamber to the exterior of said housing.

12. A sterile-loop calibration system as defined in claim 11 wherein said loop is a closed, endless loop and wherein no liquid is added to the endless loop and substantially little or no liquid is drained from the endless loop during operation of the system.

13. A system as defined in claim 11 including gas sterilizing filter means in communication with the gas injection passage for sterilizing the gas injected into the liquid passage.

14. A system as defined in claim 11 wherein said chamber includes a weir which divides said chamber into a sparging chamber section and settling chamber section, and said gas vent terminates in said settling chamber section.

15. A system as defined in claim 13 including a baffle in the sparging chamber.

16. A system as defined in claim 11 including passage means including portions of the liquid passage and the gas injection passage for forming a tee at said location in said housing.

17. A system as defined in claim 11 including pumping means including a region of the liquid passage for circulating a sterile calibration liquid through the endless path.

18. A system as defined in claim 16 wherein said location in the liquid passage is between said region of the liquid passage and the chamber and the chamber is between said location in the liquid passage and the outlet of the housing.

19. A system as defined in claim 11 wherein the liquid passage includes an outlet passage section leading to the outlet of the housing and the housing has a temperature well adapted to receive a temperature probe in heat exchange relationship with the outlet passage section.

20. A system as defined in claim 11 including a sterile calibration liquid in said loop.

21. A system as defined in claim 19 including gas sterilizing filter means in communication with the gas injection passage for sterilizing the gas injected into the liquid passage, said chamber includes a divider which divides said chamber into a sparging chamber section and a settling chamber, and said gas vent terminates in said settling chamber section.

22. A system as defined in claim 20 including passage means including portions of the liquid passage and the gas injection passage forming a tee at said location in said housing.

23. A system as defined in claim 20 including pumping means including a region of the liquid passage for circulating the sterile calibration liquid.

24. A system as defined in claim 11 wherein the gas vent includes a restricted orifice.

25. A system as defined in claim 11 including means in the gas vent for allowing gas to escape from the chamber and to substantially prevent gas from entering the chamber through the gas vent.

26. A system as defined in claim 11 wherein the liquid passage includes a radially compressible tube having a tube passage and an annular, deformable flange at one end of the tube and integral with the tube, said flange having outer and inner faces, said housing includes a first member having an opening and a flange supporting face surrounding said opening, said outer face engaging said flange supporting face with said opening being in registry with said tube passage to form a juncture of the passage and the opening, and said housing includes a tube receiving structure receiving said tube and coupled to the first member and including means defining an annular projection engaging said inner face of said flange, said annular projection being radially narrower than the inner face of the flange and providing high-unit loading of the flange to deform the flange, said annular projection urging the flange tightly against the supporting face to provide a fluid-tight seal around the juncture of the tube passage and the opening.

27. An apparatus comprising:
a housing having an inlet, an outlet, and a passage extending through the housing between the inlet and the outlet, said passage including first and second passage sections;
a curved wall surface on the housing;
a tube compressor;
said housing including a compressible tube carried by said housing and defining a portion of said passage between the first and second passage sections, said tube being between the curved wall surface and the tube compressor and being wrapped in a circumferential direction at least part way around the tube compressor;
means for mounting the tube compressor on the housing for movement relative to the curved wall to squeeze the tube in a zone which moves along the tube to thereby pump fluid in the tube;
said tube having opposite end portions which extend generally tangentially of the tube compressor and then generally axially of the tube compressor to their respective ends; and
means for sealing the ends of the tube to the first and second passage sections, respectively.

28. An apparatus as defined in claim 26 wherein the seal construction includes an annular deformable flange at one end of the tube and integral with the tube, said flange having outer and inner faces, said housing includes a first member having an opening at one end of the first passage section and a flange supporting face surrounding said opening, said outer face engaging said flange supporting face with said opening being in registry with said tube to form a juncture of the tube and the opening, said housing includes a tube receiving structure receiving said tube and coupled to the first member and including means defining an annular projection engaging said inner face of said flange, said annular projection being radially narrower than the inner face of the flange and providing high-unit loading of the flange to deform the flange, said annular projection urging the flange tightly against the supporting face to provide a fluid-tight seal around the juncture of the tube and the opening.

29. An apparatus as defined in claim 26 wherein the seal construction includes an annular, deformable flange at one end of the tube and integral with the tube, said housing having a surface surrounding one end of the first passage section and including a rigid ring, said flange being between the surface and the ring and said housing includes means contacting said ring around less than 360 degrees to squeeze the flange between the ring and the surface.

30. A method of calibrating a sensor of a sensor cassette of the type having a flow-through passage comprising:
pumping a sterile calibration liquid through a closed, endless path which includes the flow-through passage, whereby no calibration liquid is added to the endless path and substantially little or no calibration liquid is drained from the endless path during said pumping step;
injecting a sterile gas into the endless path to create a pressure in the endless path which is greater than ambient;
mixing the gas with the sterile calibration liquid in the endless path to control the partial pressure of at least a component of said gas in the sterile calibration liquid;
venting at least some of the gas from the endless path; and
exposing the sensor to the sterile calibration liquid having the controlled partial pressure of said component of said gas whereby the sensor can be calibrated.

31. A method of claim 33 wherein the step of injecting includes passing nonsterile gas through a sterilizing filter to provide the sterile gas.

32. A method as defined in claim 33 wherein said step of mixing includes passing the gas and sterile calibration liquid through a region in said endless path of increased volume.

33. A method as defined in claim 35 wherein the gas is injected into the endless path and then passed to said region of increased volume.

34. A sterile-loop calibration system comprising:
a sensor cassette having a flow-through passage and including at least one sensor to be calibrated, said sensor being responsive to a characteristic of a gas;
means defining a chamber, said chamber comprising a sparging chamber section and a settling chamber section;
means including said flow-through passage and said chamber for defining a loop;
a sterile calibration liquid in said loop, said loop providing an endless path for circulation of the sterile calibration liquid;
a gas injection passage through which a gas can be injected into the sterile calibration liquid in said loop;
means in said loop for mixing the gas and the sterile calibration liquid whereby the sterile calibration liquid and the gas can be circulated through the loop to thereby permit calibration of the sensor, said mixing means including said chamber; and
a gas vent leading from said settling chamber section to the exterior of the loop.

35. A system as defined in claim 37 including a divider which divides said sparging chamber section and said settling chamber section, and a baffle adjacent the divider and in the sparging chamber section for breaking up bubbles in the sterile calibration liquid.

* * * * *

UNITED STATES PATENT AND TRADEMARK OFFICE
CERTIFICATE OF CORRECTION

PATENT NO. : 5,057,278
DATED : October 15, 1991
INVENTOR(S) : Maxwell et al.

It is certified that error appears in the above-identified patent and that said Letters Patent is hereby corrected as shown below:

Col. 3, Line 46, "cuvette" should be --liquid--.
Col. 7, Line 68, "!19" should be --119--.
Col. 12, Line 15, "13" should be --14--.
Col. 12, Line 25, "16" should be --17--.
Col. 12, Line 37, "19" should be --20--.
Col. 12, Line 42, Before the comma insert --section--.
Col. 12, Line 44, "20" should be --21--.
Col. 12, Line 48, "20" should be --21--.
Col. 13, Line 32 (Claim 28, Line 1), "26" should be --27--.
Col. 13, Line 51 (Claim 29, Line 1), "26" should be --27--.
Col. 14, Line 23, "33" should be --30--.
Col. 14, Line 26, "33" should be --30--.
Col. 14, Line 30, "35" should be --32--.
Col. 14, Line 55, "37" should be --34--.

Signed and Sealed this

Twenty-second Day of June, 1993

Attest:

MICHAEL K. KIRK

Attesting Officer

Acting Commissioner of Patents and Trademarks